US00PP08066P

United States Patent [19]

McGredy, IV

[11] Patent Number: Plant 8,066

[45] Date of Patent: Dec. 22, 1992

[54] FLORIBUNDA ROSE PLANT NAMED MACSODA

[75] Inventor: Sam McGredy, IV, Castor Bay, New Zealand

[73] Assignee: Co-Operative Rose Growers, Inc., Tyler, Tex.

[21] Appl. No.: 704,777

[22] Filed: May 23, 1991

[51] Int. Cl.[5] ..... A01H 5/00

[52] U.S. Cl. ..... Plt./28

[58] Field of Search ..... Plt./28, 29, 20

*Primary Examiner*—Howard J. Locker

*Attorney, Agent, or Firm*—Christie, Parker & Hale

[57] ABSTRACT

A new variety of floribunda rose having bright red flowers produced in clusters.

1 Drawing Sheet

SUMMARY OF THE INVENTION

The present invention relates to a new and distinct variety of rose plant of the floribunda rose class, which was originated by my crossing as seed parent the variety known as 'Mary Sumner' and as pollen parent the variety known as 'Precious Platinum'. The varietal denomination of this new rose is 'MacSoda'.

Among the novel characteristics possessed by this new variety which distinguishes it from its parents and all other varieties of which I am aware are its attractive red flowers of pure coloration borne in small clusters on a plant suitable for growing outdoor in gardens.

Asexual reproduction by propagation by budding of the new variety as performed in Smith County, Tex. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling.

*Seed parent.*—'Mary Sumner'.

*Pollen parent.*—'Precious Platinum'.

Class: Floribunda.

The following further horticultural observations were made of specimens grown outdoor in Smith County, Tex. in the month of November.

Flower

Blooming habit: Recurrent.

A. Bud:

(1) *Size.*—Small.

(2) *Form.*—Ovoid.

(3) *Color.*—As sepals divide, near 45A to 46A.

(4) *Sepals.*—Slightly longer than bud, simple.

(5) *Peduncle.*—Length — average. Aspect — straight. Strength — erect. Color — medium green with purple cast.

B. Bloom:

(1) *Size.*—Average size when fully expanded — about 3 inches.

(2) *Borne.*—Small sprays, generally three blooms.

(3) *Form.*—Urn shaped at first, becoming flat; outer petals roll under, some quill to points.

(4) *Petalage.*—Number of petals under normal conditions — about 35 to 40.

(5) *Color.*—After sepals fall and petals unfurl, predominant flower color viewing petals' top surface is near to or somewhat darker hued than 44A. Color is substantially pure and constant on both top and undersurface of petals. Coloring tends to lighten toward orange red as flowers age with the red coloring becoming less intense. Petals are near 34C toward point of petal attachment.

C. Petals:

(1) *Texture.*—Average.

(2) *Appearance.*—Inside velvety and outside satiny.

(3) *Form.*—Acuminate.

(4) *Arrangement.*—Regularly arranged, imbricated.

(5) *Petaloids in Center.*—Few.

(6) *Persistence.*—Drop off cleanly.

(7) *Fragrance.*—Slight.

(8) *Lasting quality.*—Average.

Reproductive Organs

A. Stamens, filaments and anthers:

*Arrangement and Color.*—Regularly arranged around styles. Color — orange.

B. Pollen:

*Color.*—Yellow.

C. Styles: Even, medium length, bunched.

D. Stigmas: Cream colored.

E. Hips: Globular, medium size, orange red at maturity, seeds protrude.

Plant

A. Form: Compact.

B. Growth: Vigorous, uniform branching.

*Height attained.*—About 3 feet.

C. Foliage: Compound 3 and 5 leaflets.

(1) *Size.*—Medium.

(2) *Quantity.*—Abundant.

(3) *Color:*—New foliage: Upper side — purplish green. Under side — light green. Old foliage: Upper side — medium green. Under side — light green.

(4) *Shape.*—Oval, pointed.

(5) *Texture.*—Upper side is semi-glossy; under side is matte.

(6) *Edge.*—Serrate.

(7) *Serration.*—Ordinary, acuminate apices.

(8) *Leaf stem.*—Color — light green.

(9) *Stipules.*—Medium.

(10) *Resistance to disease.*—Blackspot — Average. Mildew — Above average.

D. Wood:

(1) *New wood.*—Color — purple green. Bark — smooth.

(2) *Old wood.*—Color — medium green. Bark — smooth.

E. Thorns:

(1) *Thorns.*—Quantity (main stalk) — ordinary. On laterals from stalk — few. Form — flat base. Length — small. Color — purple when young. Position — irregular.

(2) *Prickles.*—Profuse to average on main stalks and laterals.

F. Winter hardiness: Winter hardy but needs protection in severe climates.

I claim:

1. A new and distinct variety of rose plant of the floribunda rose class, substantially as shown and described.

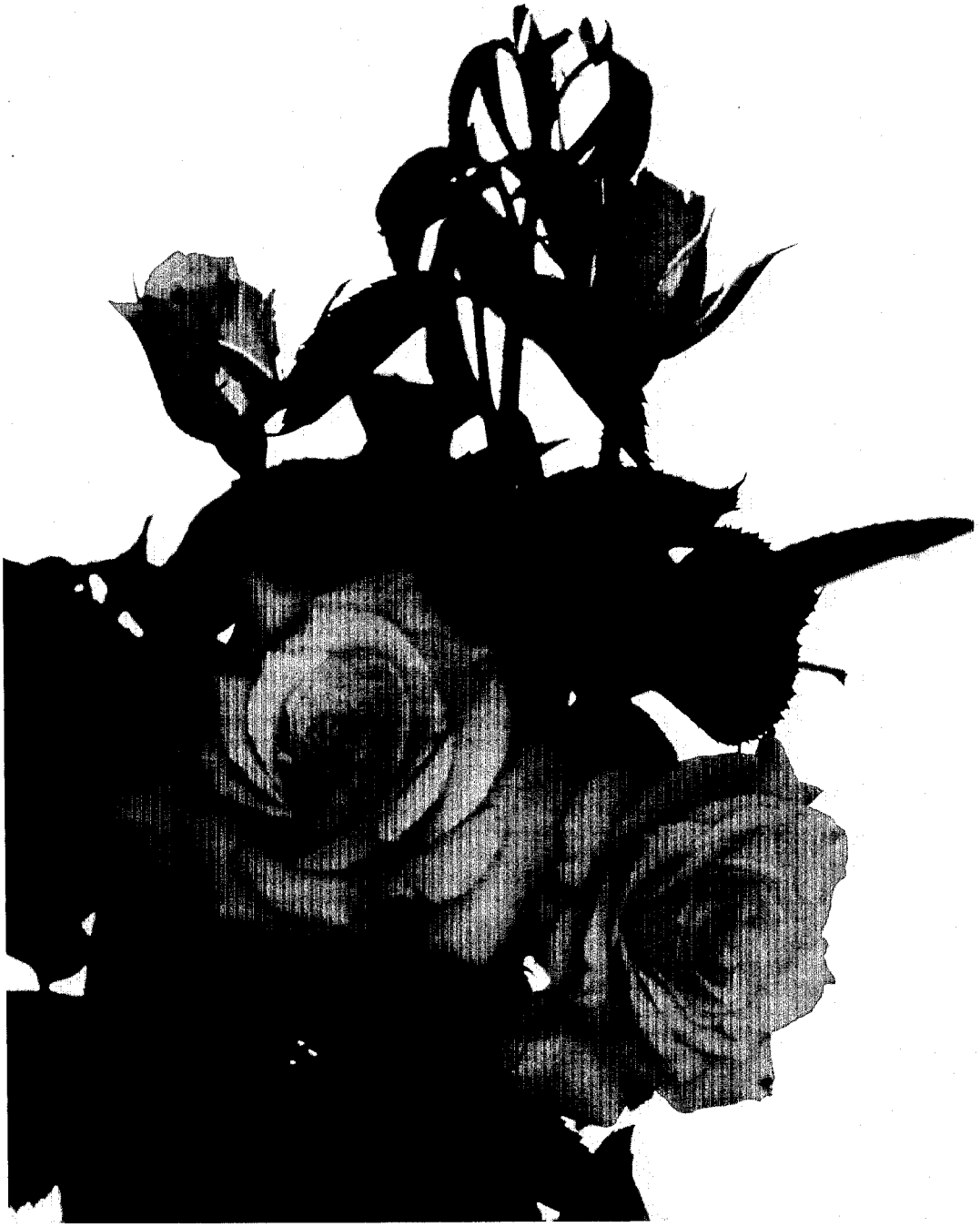

* * * * *